US008638295B2

(12) United States Patent
Bruss et al.

(10) Patent No.: US 8,638,295 B2
(45) Date of Patent: Jan. 28, 2014

(54) CONTROL CONFIGURATION FOR DIGITAL IMAGE SYSTEM

(75) Inventors: Andrew Bruss, Easley, SC (US); Maura Ann Bidinost, Canonsburg, PA (US); Tony Melanson, Pittsburgh, PA (US)

(73) Assignee: Omnyx, LLC, Pittsburgh, PA (US)

( * ) Notice: Subject to any disclaimer, the term of this patent is extended or adjusted under 35 U.S.C. 154(b) by 272 days.

(21) Appl. No.: 13/233,510

(22) Filed: Sep. 15, 2011

(65) Prior Publication Data

US 2012/0068928 A1  Mar. 22, 2012

Related U.S. Application Data

(60) Provisional application No. 61/383,555, filed on Jun. 16, 2010.

(51) Int. Cl.
*G06F 3/033* (2013.01)

(52) U.S. Cl.
USPC ............................. 345/157; 345/163; 345/167

(58) Field of Classification Search
None
See application file for complete search history.

(56) References Cited

U.S. PATENT DOCUMENTS

| 6,727,884 | B1 | 4/2004 | Leatham et al. |
|---|---|---|---|
| 6,757,002 | B1 | 6/2004 | Oross et al. |
| 7,369,117 | B2 | 5/2008 | Evans et al. |
| 7,596,249 | B2 | 9/2009 | Bacus et al. |
| 8,214,539 | B1 * | 7/2012 | Kulanko ........................... 710/5 |
| 2006/0082600 | A1 | 4/2006 | Odagawa |
| 2006/0152495 | A1 | 7/2006 | Gombert |
| 2006/0264746 | A1 | 11/2006 | Frisa et al. |
| 2008/0154573 | A1 | 6/2008 | Jarrett et al. |
| 2008/0250429 | A1 | 10/2008 | Lockhart et al. |
| 2010/0199229 | A1 | 8/2010 | Kipman et al. |
| 2010/0225668 | A1 | 9/2010 | Tatke et al. |
| 2010/0260407 | A1 | 10/2010 | Eichhorn et al. |

OTHER PUBLICATIONS

International Searching Author, Search Report for International Application PCT/US2011/051851, Dec. 23, 2011 (EPO), 2 pages.
Available at http://web.archive.org/web/20080509064035/http://www.traxsys.com/. Welcome to Traxsys, 1 page, May 9, 2008.
Available at http://web.archive.org/web/20100720024354/http://www.bioimagene.com/products_solutions/input_devices/islide.html, iSlide Input Device, 2 pages, Jul. 20, 2010.
Catalyurek, U., et al., "The Virtual Microscope," IEEE Transactions on information Technology in Biomedicine, Dec. 2003, 17 pages, vol. 7, Issue 4. Online at www.cs.umd.edu/Library/TRs/CS-TR-4405/CS-TR-4405.pdf.

(Continued)

*Primary Examiner* — Jason Olson
(74) *Attorney, Agent, or Firm* — Ronald Law Group, LLC; Carl A. Ronald

(57) ABSTRACT

Systems, methods, and products are described that provide control configuration for a digital image system. One aspect provides for a system configured to identify one or more input control devices in communication with a digital image application operating on said system, the one or more input devices comprising one or more control elements; activating an input control device mode based on a number of identified input control devices; and mapping the one or more control elements of each input control device to one or more digital image application functions based on a type of the input control device and the input control mode. Other aspects and embodiments are also described herein.

20 Claims, 17 Drawing Sheets

(56) References Cited

OTHER PUBLICATIONS

3D Histech, Pannoramic Viewer 1.14, 67 pages, User's Guide, Rev. 1, May 10, 2010.

Logitech, Wireless Trackball M570, Customizing by G700 with Logitech software (SetPoint), 9 pages. Website captured at http://logitech-en-amr.custhelp.com/app/answers/detail/a_id/18287 on Aug. 27, 2012. Published on website Aug. 31, 2010.

* cited by examiner

US 8,638,295 B2

CONTROL CONFIGURATION FOR DIGITAL IMAGE SYSTEM

CROSS REFERENCE TO RELATED APPLICATION

This application claims the benefit of U.S. Provisional Patent Application Ser. No. 61/383,555, entitled "Control Configuration for Digital Pathology Workstation," filed on Sep. 16, 2010, the contents of which are incorporated by reference as if fully set forth herein.

BACKGROUND

Pathology is an important medical specialty involving the study and diagnosis of disease through the examination of bodily specimens. Conventional specimen examination procedures involve viewing glass specimen slides through an optical microscope. Digital pathology allows pathologists to examine digital specimen slides generated by scanning physical glass slides using a digital scanner. In general, the digital specimen slides are stored in some form of database and are accessed through a computing device interface in communication with the database. Examining and manipulating specimen slides in a digital pathology environment involves a set of operations different than those used according to conventional methods.

BRIEF SUMMARY

In summary, one aspect provides a system comprising: one or more processors; a memory in operative connection with the one or more processors; wherein, responsive to execution of program instructions accessible to the one or more processors, the one or more processors are configured to: identify one or more input control devices in communication with a digital image application operating on said system, the one or more input devices comprising one or more control elements; activate an input control device mode based on a number of identified input control devices; and map the one or more control elements of each input control device to one or more digital image application functions based on a type of the input control device and the input control mode.

Another aspect provides a method comprising: identifying one or more input control devices in communication with a digital image application operating on a computing device comprising one or more processors operatively connected to a memory, the one or more input devices comprising one or more control elements; activating an input control device mode based on a number of identified input control devices; and mapping the one or more control elements of each input control device to one or more digital image application functions based on a type of the input control device and the input control mode.

A further aspect provides a computer program product comprising: a computer readable storage medium having computer readable program code embodied therewith, the computer readable program code comprising: computer readable program code configured to identifying one or more input control devices in communication with a digital image application, the one or more input devices comprising one or more control elements; computer readable program code configured to activate an input control device mode based on a number of identified input control devices; and computer readable program code configured to map the one or more control elements of each input control device to one or more digital image application functions based on a type of the input control device and the input control mode.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
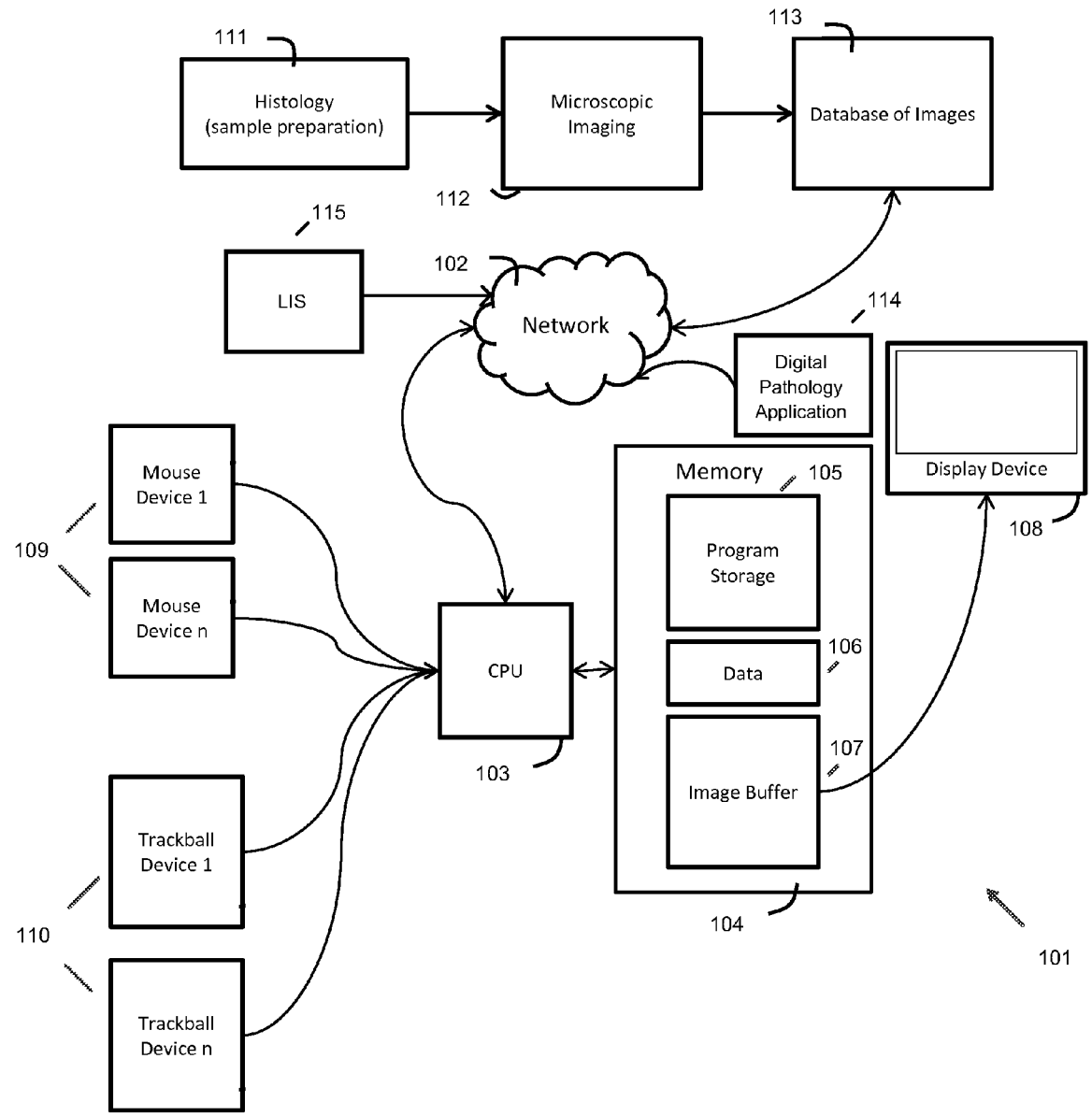
FIG. 1 provides an example digital pathology system configured to operate with multiple control devices according to an embodiment.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail to avoid obfuscation.

According to conventional methods, pathologists examine physical specimen slides using an optical microscope. Recent advances provide for digital pathology systems wherein digital images are examined using a computing device display. Primary advantages of digital pathology systems include improved access to specimens and enhanced functionality for examining specimen slides. In addition, some tasks associated with the handling of slides and the manual manipulation of optical instruments according to conventional methods may be obviated in a digital pathology system. Computerization of the workflow steps involved in generating and examining specimens operates to improve the integrity of the process, for example, by reducing issues associated with lost or missing slides, scheduling reports, and mishandling of reports.

Collecting and presenting digital specimen image data involves multiple technical challenges. For example, encoding images spanning a single specimen sample, each requiring a high magnification and a high resolution appropriate for diagnosis, requires a large volume of data. Each captured image may encompass a small area of the specimen sample at a high magnification in the form of a scanned strip or mosaic tile. However, specimen samples need to be made available for viewing by the pathologist over their full area, perhaps requiring the ability to pan from one point on a particular captured image to another point captured on a spatially adjacent image.

Digital specimen images are typically generated using specimen slide imaging scanners. During scanning, data processors handle automatic focusing and the merging of pixel data across borders present where adjacent image capture frames abut, for example, as tiles or strips. Mass data memory stores the many gigabytes of image data that are typically generated. Servers and data communication networks organize and serve up selected images while associating the images with patient cases and accepting input from reviewing pathologists.

A digital pathology workstation may be configured to utilize one or more processors and software routines to present selected images on a display device and provide image manipulation functions controlled by input control devices. In addition, digital pathology computer systems may be integrated through data communications to one or more a patient or laboratory information systems and may support other associated functions, such as document handling, accounting and the like. An exemplary digital pathology system has been disclosed in U.S. patent application Ser. No. 12/554,276, filed on Sep. 4, 2009, the contents of which are incorporated by reference as if fully set forth herein.

The typical pathologist is experienced with viewing specimen slides using some form of optical microscope. When examining a specimen slide, a pathologist might shift between alternative microscope objective lenses to change magnification. The specimen slides may also be physically moved around the microscope stage, for example, to pan over the specimen area. However, examining images in a digital pathology environment according to existing technology does not provide the same mechanisms for viewing and manipulating specimen samples. Nonetheless, pathologists do not want to sacrifice the advantages provided by digital pathology systems, which facilitate dynamic and powerful computing operations on digital specimen images and associated data, but are generally not like using an optical microscope In addition, different users may access digital images using different workplace configurations. For example, certain pathologists may use a dedicated digital pathology workstation, which may include dual displays and other hardware and software configurations useful for controlling digital images and associated data. On the other hand, other pathologists, or the same pathologist operating at a remote workstation, may access the same images and information using a general purpose computer that does not have dedicated digital pathology hardware or software. However, existing technology does not provide systems or methods for serving digital pathology system users optimally at various workstations with different hardware and software configurations.

Embodiments may be configured to optimally facilitate the interaction of a user with a system structured to provide access to digital images. Embodiments provide that the digital images may be derived from specimen samples, including, but not limited to, digital specimen slides derived from glass specimen slides prepared in a histology laboratory. According to embodiments, control of digital image presentation may be configured to optimize image viewing and manipulation by adapting control operations based on the characteristics of the computing device accessing the digital images. Non-limiting examples of characteristics include hardware components and associated configurations, software, type of operating system, number of display devices, and number and type of input control devices (e.g., mouse, trackball, or both).

The manipulation of digital images has certain advantages over conventional methods, including the ability to zoom continuously through higher or lower magnification and to apply certain processing operations to image pixel data. However, conventional methods, such as using an optical microscope to view a glass specimen slide, are well known in relevant fields such as pathology, and provide an intuitive environment for viewing specimen samples. Embodiments may be configured to emulate conventional operations for interacting with specimen samples within a digital specimen image environment. A non-limiting example provides that digital image presentation may be configured according to embodiments to emulate viewing and manipulating digital specimen images using a conventional optical microscope. According to embodiments, emulated image viewing operations may be configured to operate in conjunction with digital image manipulation operations, including, but not limited to, zoom, pan, rotate, annotate, image access, and variations thereof (e.g., continuous pan).

Digital image manipulation functions and emulation operations may be controlled through one or more input devices configured according to embodiments. An illustrative and non-restrictive example provides for controlled input devices with cursor or pointer positioning capabilities and selectively operable input switches that may be regarded as redundant but may be made functionally distinct. Embodiments provide for multiple control devices in the form of pointing devices, including, but not limited to, a trackball input device comprising functions associated with digital image manipulation operations, and a mouse input device comprising functions associated with general computing tasks.

Referring now to FIG. 1, therein is depicted an example digital pathology system configured to operate with multiple control devices according to an embodiment. A digital pathology workstation 101 is operatively coupled to a database of images 113 through a network 102. Digital pathology workstation software 114, such as a digital pathology system client application, operable on or in association with the digital pathology workstation 101 may be arranged to access the database of images 113 and an associated information system, such as a laboratory information system (LIS) 115.

Images stored in the database of images 113 may be comprised of digital pathology images generated through an imaging system 112, for example, a robotic whole slide microscopic camera imaging system. The targets of the imaging may be tissue specimens, for example, from biopsies or cytologic swab procedures, prepared in a histology operation 112 and stored as digital data files in a database of images 113. In the example illustrated in FIG. 1, the database of images 113 is remote from the digital pathology workstation 101 and is accessed over a network 102, such as a LAN or WAN network or over the Internet. The workstation 101 may be one of many workstations, such as a group of workstations in a clinical pathology laboratory, having access to the database of images 113, as well as associated medical information.

The workstation 101 may include a central processing unit (CPU) 103 operatively coupled to a memory 104. The memory 104 may comprise program storage 105 (e.g., executable machine instructions), a data memory 106 for variable values, and one or more memory sections that function as image buffers 107 (e.g., addressable memory for storing pixel data). As shown in FIG. 1, the image buffers may operate to transmit data, such as pixel data to a display device 108 operatively coupled to the digital pathology workstation 101. In a non-limiting example, the pixel data may include RGB, luminance-saturation-hue, or similar color definitions for pixel data utilized during operation of the digital pathology workstation 101. Illustrative and non-restrictive examples of pixel data include pixel data in data files containing images stored in the database of images 113, points displayed on the visual display 108, CPU 103 data communication, or intermediate version of such pixels, wherein the values may be adjusted by processing.

As shown in FIG. 1, one or more input control devices 109, 110 may be coupled to the CPU 103 for performing certain operations on the digital pathology workstation 101. For example, the input control devices 109, 110 may be configured to separately or jointly control manipulation of the pixel data and to perform generic computing functions. In the example depicted in FIG. 1, one or more input control devices are provided in the form of one or more mouse devices 109 and one or more trackball devices 110.

Embodiments provided herein are not limited by the input control device configuration of FIG. 1. For example, embodiments may be comprised of solely one mouse device, solely one trackball device, one trackball device and one mouse device, single or multiple mouse and trackball devices in combination, or in combination with other types of input control devices, or any other combination of input control devices capable of operating according to embodiments described herein. Alternative and exemplary input control devices include, without limitation, keypads and keyboards, game controllers, touchpads, joysticks, components configured to emulate certain devices (e.g., microscopes), and any other input control device capable of enabling position or direction selection. As used herein, the term trackball device may be directed toward conventional trackball input devices, trackball components of trackball devices, or other devices or device components continuously displaceable as opposed to selecting a point between endpoints. In addition, the examples used in this disclosure are solely for purposes of illustration, and do not exclude any other input, switch, or selection device capable of controlling computing devices and their displays.

In FIG. 1, selection using the one or more input control devices 109, 110 may be made by manual contact or movement. Non-limiting examples of selection actions include the following: pressing a switch, pressing a switch intermittently or in a sequence or code; rolling a continuously movable roller, ball, or displacement sensor, which may be exposed or concealed; rotating, inclining, pushing, or pulling a control shaft; moving a finger tip or contact element around a field; and moving or pressing a bezel. In addition, embodiments provide for alternative input control devices that are voice controlled or activated by a signal from another device, such as an infrared signal source. According to embodiments, interpretation of commands intended by digital pathology workstation 101 users requires the CPU 103 to process signals received from the input control devices, discerning the device that has been operated by the user, and the particular input function that has been invoked.

A computing device and associated software configured according to embodiments may selectively provide functionality and perform operations based on the number and type of detected input control devices. Embodiments provide that the input control device configuration may be established based on the hardware elements sensed to be present on the computing device. According to embodiments, the detection process may be conducted responsive to certain events, including, but not limited to, registering new hardware, computing device startup, operating system startup, or application startup, especially for mouse and trackball pointing devices.

Figure 2:
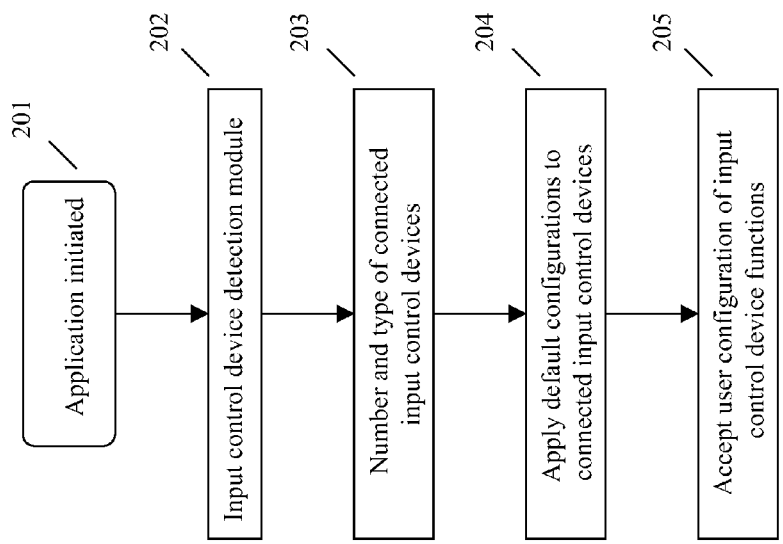
FIG. 2 provides an example input control device detection and configuration process.

Referring now to FIG. 2, therein is depicted an example input control device detection and configuration process for a digital image manipulation application arranged according to an embodiment. The application is initiated 201, which launches an input control device detection module 202. The input control device detection module operates to detect the number and type of input control devices connected to the computing device 203. A device mapping module operates to apply default configurations, if available, to detected input control devices 204. As a non-limiting example, if a trackball device is detected, the application may set the trackball element to perform, inter alia, continuous pan operations on digital images. The device mapping module offers options for user configuration of input control device functions 205, such as mapping particular buttons to particular functions, which allows for accommodation of user preferences. For example, a user may arrange a left-handed configuration of an input control device that is configured as a right-handed device by default.

Embodiments may be configured to process raw input control device input. In order to map events from input control devices, such as trackball and mouse input devices, independently, detailed device information must be gathered according to embodiments. In a typical operating system, such as the Windows® XP operating system, certain input device information is accessible by applications. Windows® is a registered trademark of the Microsoft Corporation in the United States, other countries, or both. For example, Windows® operating systems provide the Windows® Presentation Foundation (WPF), which may provide device information. However, systems configured according to embodiments may require more detailed information than typically provided by operating systems, such as through WPF.

Windows® operating systems provide an API that allows applications to receive input events before any application-level processing has occurred. The API provides two main functions utilized according to embodiments: (1) a list of devices, including input control devices, connected to the system, and (2) delivery of raw input events for further processing.

Digital pathology systems provide many advantages over conventional specimen examination methods. However, certain traditional methods, such as viewing physical specimen slides under an optical microscope, may be simpler and more familiar to users, such as pathologists. Accordingly, embodiments are configured to emulate conventional specimen examination methods in conjunction with providing advantageous operations available through digital image systems. Exemplary embodiments are directed toward emulating an optical microscope within a digital image environment using one or more input control devices, such as a digital pathology or histology environment.

According to embodiments, a trackball input control device may be configured to emulate an optical microscope by mapping the trackball device to the specimen image display. In addition to traditional trackball devices, embodiments may be configured to operate with other devices that, like a trackball device, are continuously displaceable as opposed to providing selection between endpoints. In emulating the pathologist's two-dimensional displacement of a glass slide on a microscope stage, the input of a trackball device configured according to embodiments may be used, for example, for pan functions to navigate digital images. Certain embodiments provide for a trackball device that may be arranged to cause displacement of a cursor or the panning of a displayed image which continues beyond the extent of a currently loaded frame. Panning of an image up to a current frame border, for example, by rolling a trackball control, operates according to embodiments to queue the loading of the next adjacent frame. Panning navigation in any direction proceeds up to and beyond the border of the current image frame and into and through the next adjacent image frame and so on, up to the ultimate border of the complete specimen image that is comprised of stitched adjacent image capture tiles or strips. In addition, embodiments provide that panning functions may be mapped to or invoked using one or more alternative positioning devices that may operate with or without a displayed cursor function, such as a mouse or keyboard.

Digital zoom is generally not an aspect of manually operated optical microscopes, which typically use a carousel or other mechanism allowing the substitution of objective lenses to change magnification. Embodiments provide for mapping input control device functions to provide digital zoom within the image manipulating environment. Non-limiting examples provide for mapping a roller wheel of a trackball device, the scroll wheel of a mouse, switch entry selection, or menu item selection to a digital zoom function. According to embodiments, continuous zoom-in and zoom-out capabilities may be mapped to input control device functions to provide for re-displaying an image, either centered on the image or on a cursor location. Embodiments provide that re-displaying at different magnifications (zooming) may select among discrete predetermined magnifications and resolutions, may be continuously adjustable, or may produce incremental stepwise changes in magnification.

As previously mentioned, the digital images described herein generally involve large data files, which require time and computing load when passing through intermediate magnifications. Another exemplary operation involves movement of the scroll wheel quickly in either direction, which may be configured according to embodiments as an instruction to jump to a minimum or maximum magnification, or to progress by more than the next sequential increment, obviating the loading of intermediate magnifications. Certain embodiments provide for the configuration of keyboard shortcuts, either alone, or in combination with input device functions, for jumping directly to or between specified magnifications in any desired order.

Figure 3:
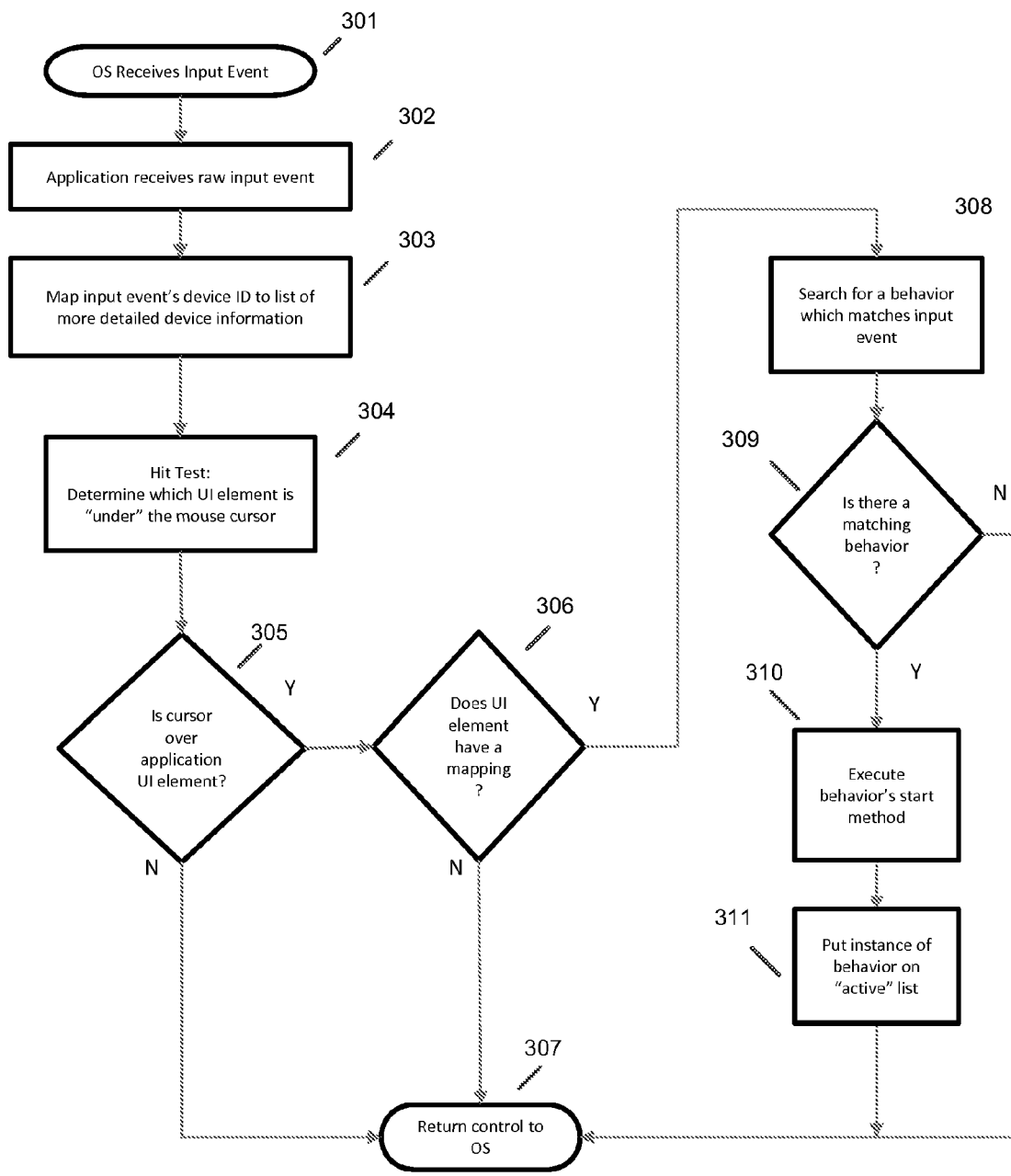
FIG. 3 provides an example process for mapping and executing an input control device behavior.

FIG. 3 provides an example flowchart for mapping and executing an input control device behavior (e.g., application function) according to an embodiment. The operating system (OS) receives an input event 301 from an input control device and the application receives a raw input event 302. The device producing the input event is mapped to a list of more detailed device information 303, which may include a list of all possible devices and switched or otherwise generated inputs, which may entail determining which switch of which device has been operated. A "hit test" operates to determine which user interface (UI) element is "under" the mouse controller 304. As a non-limiting example, the hit test may determine whether a selection has been primed, for example, because a cursor associated with the device is currently positioned over a displayed selection.

If the cursor is over an application UI element 305, the example illustrated in FIG. 3 may be configured to determine whether the UI element has a mapping 306. If the cursor is over an application UI element 305 and the UI element has a mapping 306, a search may be performed to locate a behavior which matches the input event 308; otherwise control is returned to the OS 307. For example, if a click button is operated when no selection is primed or indicated, the click operation is ignored and control is returned to the OS. If there is a matching behavior, or application function, for the input event 309, the behavior's start method is executed 310; otherwise, control is returned to the OS. Subsequent to executing the behavior's start method 310, an instance of the behavior is placed on an "active" list 311 and control is returned to the OS 307.

Input signals received by applications configured according to embodiments may be mapped or associated with functions according to the programmed operation of the CPU. Embodiments provide that input devices may include USB devices with encoded identifications and codes used by a programmed CPU, for example, to distinguish the respective devices and the respective switches or other input signals generated by each given device. Responsive to initial set-up functioning or when a new user input device is coupled to the workstation, embodiments may be configured to operate a registration process whereby devices and device inputs may be recognized. Thereafter, embodiments provide that the switch inputs may individually or by combined or sequenced operations invoke functions with which the CPU may be programmed to associate mapped switch inputs, combinations, sequences, or variances thereof, with particular functions.

Operation of input control device switches and other inputs configured according to embodiments may be associated with prompting messages, menus, and similar indications. An input control device configured according to embodiments may effect a cursor to be positioned over a displayed option selection area and arranged to invoke a function if a switch is operated when the cursor is in that position. Embodiments may be further configured to allow a user to displace the cursor using the input control device and to select a different option.

Figure 4:
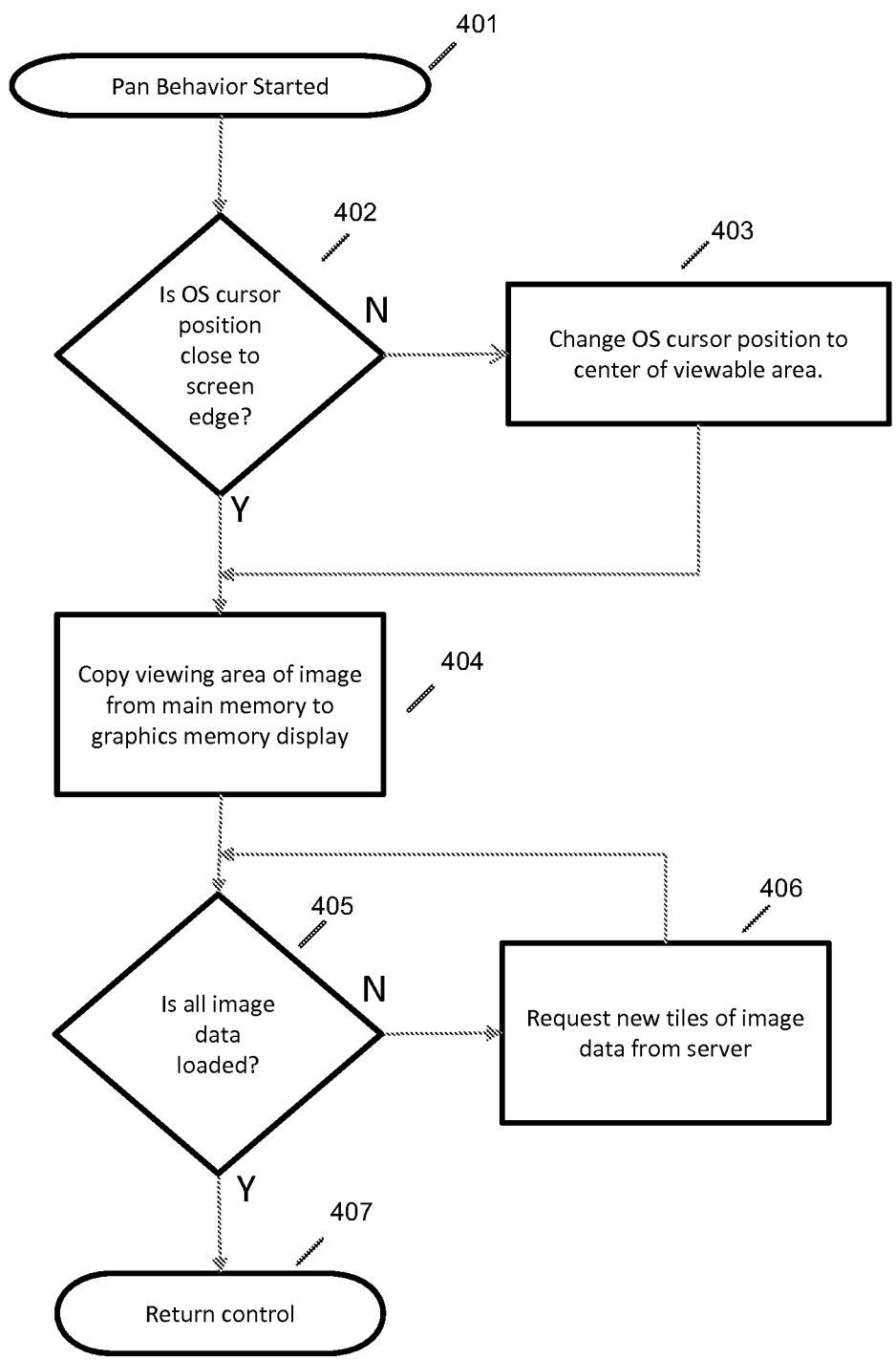
FIG. 4 provides provided an example image pan behavior process.

Referring to FIG. 4, therein is provided an example process effected when a behavior associated with an operation is selected according to an embodiment, particularly continuous pan behavior. Specific inputs may include, but are not limited to, a pulse or pulse train from the left/right or up/down rotation encoder of a trackball or mouse. The process illustrated in FIG. 4 may be arranged according to embodiments to move either the cursor across the display or to move the image of the subject across the display area, or a combination thereof. In addition, embodiments provide that the input device may be used to select between different operational modes. Illustrative and non-restrictive examples of operational modes include a normal mode, wherein the switch input moves the cursor over the display area, and a scroll mode, wherein the same input signal is interpreted to dictate that the displayed image is to be scrolled in one direction or another across the display screen to the border of the display area.

As provided in FIG. 4, when the pan behavior is started 401, the position of the operating system cursor on the currently displayed page is assessed, and the process determines whether the OS cursor position is close to the screen edge 402. If the cursor is not close to the screen edge 402 and there is room to move the cursor, the cursor is moved; otherwise, panning may operate to pan the displayed image across the displayed area and to center the cursor position at the center of the viewable area and 403. If the cursor is close to the screen edge 402, the viewing area of the image from main memory may be copied to a graphics memory 404, for example, by re-copying a portion of the current image frame to the display memory such that the current image is placed further along in the direction of panning. Subsequent to copying the viewing area of the image from main memory 404, the process determines whether all image data has been loaded 405. If all of the image data has been loaded 405, control is returned to the OS 407; otherwise, new tiles of the image data are requested from the server 406.

When panning over a digital image, embodiments may be configured to save in the local computing device an image buffer comprising some or all of the pixel data of the digital image and any related information (e.g., case and digital image records). The data may be retained locally, for example, until the case record or digital image is closed. Saving the data locally allows the same area to be reviewed again, optionally at different magnification, without the need to retrieve the image again from a remote source.

According to embodiments, emulation of an optical microscope may comprise arranging one or more panning functions which involve displacing the displayed image relative to the display screen using an input control device, such as a trackball or similar position indicating device. Embodiments provide that the direction and extent of displacement of a panned image may be related to the direction and extent of displacement of the trackball or similar device. The relative distance of displacement of images being displayed through an application configured according to an embodiment may be less at lower levels of magnification and greater at higher levels of magnification. Such translation of movement to magnification level additionally emulates the operation of an optical microscope in a digital image environment. According to embodiments, options may be configured such that inversion or scaling of the extent of displacement may be associated with certain input control device functions, such as trackball movement. For example, embodiments may be configured to pan a distance calculated by applying a ratio or other factor based on the magnification level to the displacement of the trackball or similar device.

Certain embodiments may emulate the inversion of an image by exemplary optical microscopes. A non-limiting example provides for presenting a user with a digital image on a virtual microscope stage such that displacing the digital image on the virtual microscope stage in a particular direction produces displacement in the opposite direction. Such inverted movement emulates the inversion of an image by exemplary optical microscopes. In addition, embodiments may be configured to emulate slide navigation on an optical microscope. In an illustrative and non-restrictive example, a user may customize an input control device, such as the trackball element of a trackball input device, to emulate the ability to move a slide freely about the stage of an optical microscope. According to embodiments, the trackball axis may be mapped and the trackball element locked in a "stage" mode such that users may be guided to view an image in a straight down-across-up-across pattern, emulating the movement of a slide on an optical microscope.

Panning a glass specimen slide on an optical microscope provides a continuous view of the specimen until the end of the slide is reached. However, digital specimen slides generated according to existing technology consist of multiple scanned strips or a mosaic of image tiles. Panning functions initiated using input control devices operatively coupled to computing devices and applications configured according to embodiments may continue indefinitely in any direction, although the displayed image frame and the stored collage of adjacent image frames may not be infinitely long. At the point that a moved cursor encounters the edge of a currently loaded image frame, it would normally be necessary to scroll the border of the image into the display area, or perhaps to stop scrolling.

Embodiments provide that when panning, scrolling, or moving a cursor across the display beyond the displayed portion of the image frame or beyond the image frame itself, the system may be arranged to retrieve the next captured image frame beyond the frame that is currently displayed. According to certain embodiments, panning at least to a point approaching the border of a currently viewed image frame or image file may cause the programmed CPU to queue up the next adjacent image file. As such, embodiments provide for the panning of digital images using input control devices, wherein panning may proceed endlessly, up to the border of the extreme edge of a composite image that potentially comprises a long succession of adjacent tiles or strips.

Zooming, like panning, may be accomplished according to embodiments by regenerating the displayed image pixel data stored in the image buffer after manipulation of pixel data in the remote image data store, at least one memory buffer accessible to the CPU, and the image buffer memory storing the currently displayed image. In addition, certain embodiments provide that when image pixel data stored at a workstation local memory includes higher and lower resolution areas, different resolution images that are available may be selected when zooming. According to embodiments, when the pixel data is all stored at a high resolution, zooming out may comprise rescaling the pixel data available at high resolution to a lower resolution corresponding to the number of pixel positions in the display image buffer. This process may involve decimating or averaging the pixel data values, to scale the available data to the corresponding pixels. For zooming in, embodiments provide for interpolating pixel values from the previous values in the display memory. However, resolution may be lost. As such, embodiments may be configured to zoom in by retrieving from the local memory or from the remote image store a new image frame at a higher resolution, and processing that higher resolution to the available number of pixels in the display.

An exemplary embodiment provides that zooming in or out may comprise re-copying the image from the main memory to the graphics display image buffer. When zooming in, the pixel data may simply be recopied, potentially with scaling to a required resolution. When zooming out, there is a possibility that the image to be displayed is larger than the composite of frames currently stored in the main memory. As such, when necessary, new frames may be obtained, for example, over a network, from a server, a mass memory, or some combination thereof, where images are stored.

Figure 5:
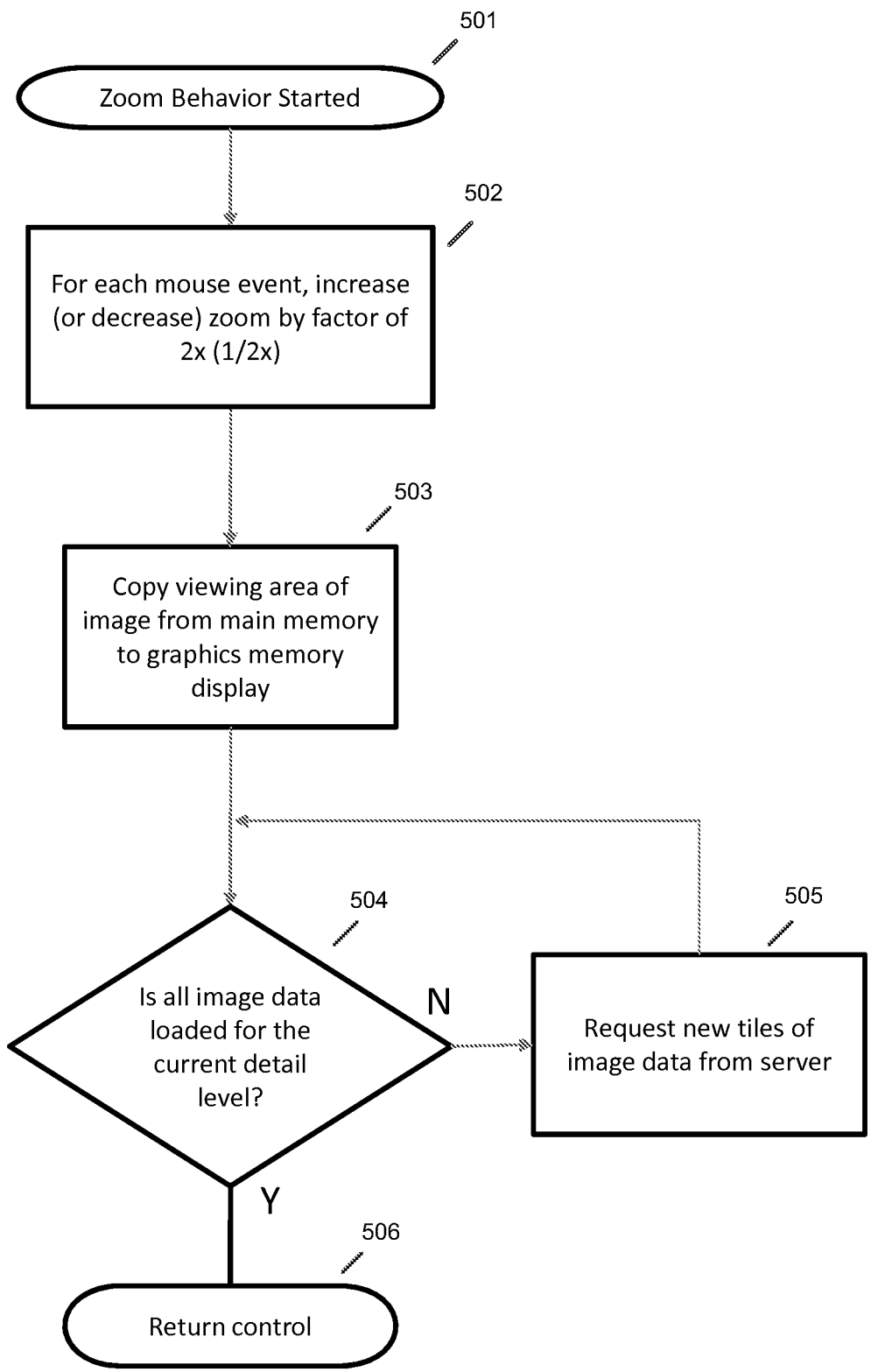
FIG. 5 provides an example zoom behavior process.

FIG. 5 provides an example zoom behavior process configured according to an embodiment. A zoom behavior (increasing or decreasing magnification) is initiated 501 by a mouse input control device. For each mouse event, the zoom factor is increased or decreased accordingly by a zoom factor 502. In the example depicted in FIG. 5, the zoom factor is 2× for increased magnification and ½× for decreased magnification. The viewing area of the image from main memory is copied to the graphics memory display 503. If all of the image data is loaded for the current detail level 504, control is returned to the OS 506; otherwise, a request for new tiles of image data from the server is initiated 505.

A non-limiting example of a mouse event for the process provided in FIG. 5 may be activation of a mouse scroll wheel, such that scrolling in the forward direction increases magnification and scrolling in the opposite direction decreases magnification. In addition, another non-limiting example of the process shown in FIG. 5 involves zoom behavior effected stepwise in multiples of two, especially when a pushbutton switch is mapped to the zoom command. In this example, a zoom-in command increases the pixel resolution by a factor of two and a zoom-out decreases the pixel resolution by the same amount.

Figure 6:
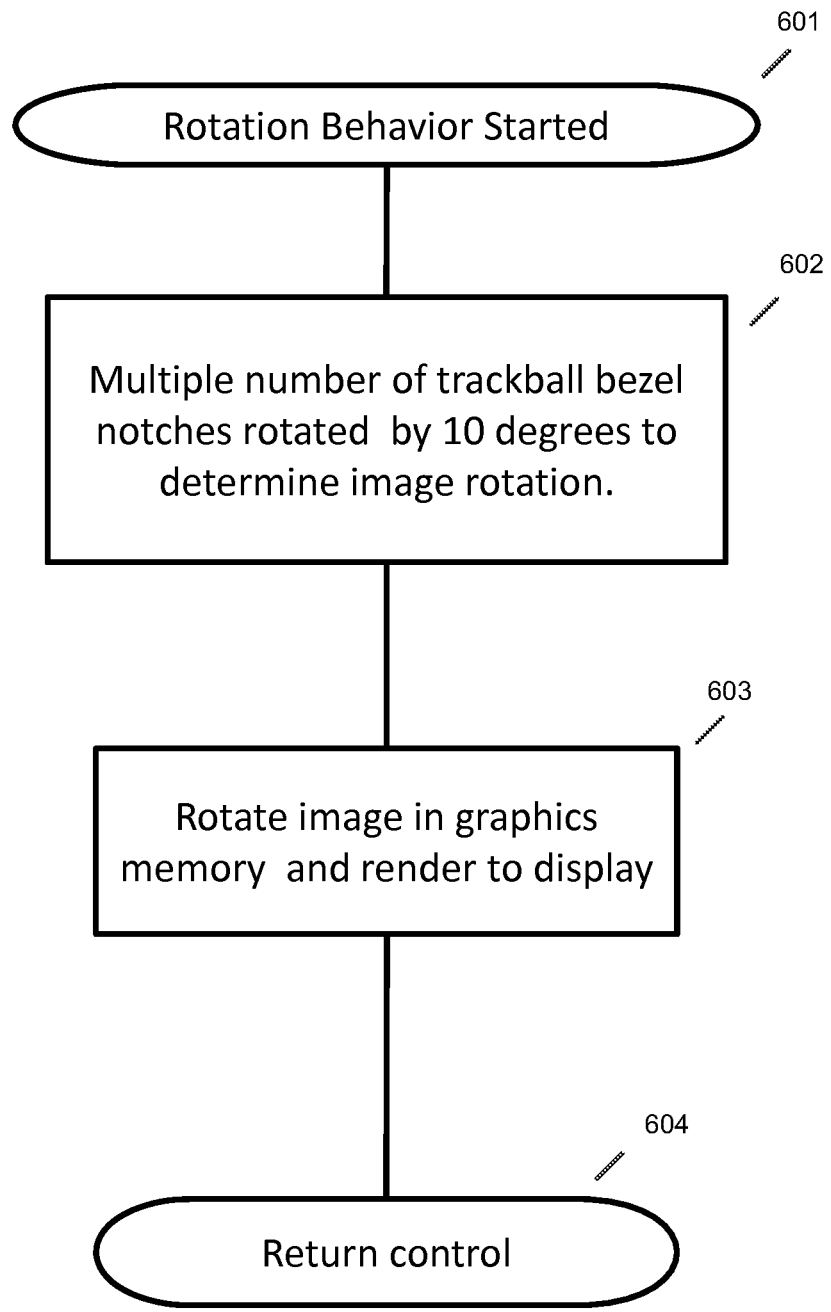
FIG. 6 provides an example process for rotating digital images.

Referring to FIG. 6, therein is provided an example process for rotating digital images according to an embodiment. A rotation behavior is started 601, and the number of rotational degrees are determined 602. In the example of FIG. 6, the rotation behavior involves a multiple number of trackball bezel notches being rotated 10°. The subject image in graphics memory is rotated and rendered to the display 603 and control is returned to the OS 604.

According to embodiments, rotation may be invoked, for example, by rotating a trackball bezel ring as the input mechanism, which may result in the recopying of the image to the display image buffer with an angular offset. To emulate manual operation of a microscope, embodiments provide that the rotation of the image may be matched to the angle of rotation of a bezel ring or similar rotational input device, or some ratio thereof. Embodiments may be configured to provide rotation mapped to a switch input. A non-limiting example provides that each successive operation of the switch may invoke incremental rotation, for example by ten degrees. Rotation alone generally does not necessitate retrieval of additional image frames. However, for images displayed using a typical rectangular 4×3 or 16×9 aspect ratio, it may be necessary to retrieve additional image frames when rotation places an area of the image that has not yet been loaded onto a corresponding part of the screen.

Figure 7:
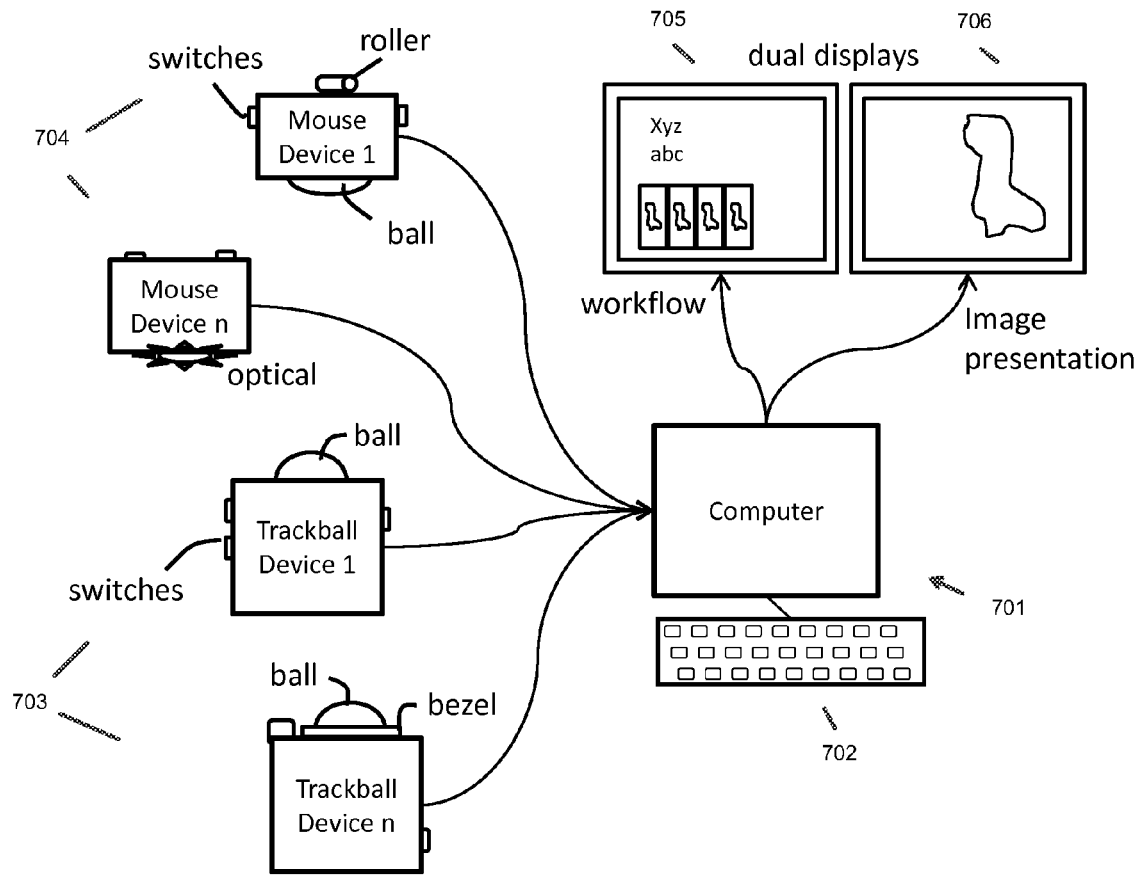
FIG. 7 provides an example workstation connected to multiple input control devices according to an embodiment.

FIG. 7 provides an example workstation connected to multiple input control devices according to an embodiment. A computer workstation 701 is connected to a keyboard 702, one or more trackball input devices 703, and one or more mouse input devices 704. Dual monitors 705, 706 are also connected to the computer workstation 701. In the example embodiment illustrated in FIG. 7, the input devices 703, 704 and displays 705, 706 are operated under control of the computer workstation 701 programmed processor in a manner that optimizes the different display functions presented on the different displays 705, 706.

As shown in FIG. 7, the left display 705 is dedicated primarily to presenting images and information related to workflow computing functions, including, manipulating text and thumbnail views, data entry, accessing files and related information. The right display 706 is dedicated primarily to image presentation and manipulation, for example, viewing, manipulating, and navigating high resolution images, including panning, zooming, rotating, and annotating. Each display 705, 706 may be comprised of different specifications, especially with the image presentation display 706 having a greater number of pixels, perhaps on a larger display area, with better specifications such as color accuracy, high refresh frequency and low persistence (less smearing when panned).

The input devices 703, 704 presented in FIG. 7 may be mapped to certain functions operative on the computer workstation 701. A non-limiting example provides that the one or more trackball input devices 703 may be mapped to image presentation and manipulation functions, such as those accessed through the left display 705, while the one or more mouse input devices 704 may be mapped to the workflow computing functions accessed through the right display 706.

The example mouse and trackball devices 703, 704 of FIG. 7 are depicted in various configurations. Embodiments provide that such devices may be more or less complex, or provided with different complements of switches and other inputs. According to embodiments, input control devices that are available may be assigned to different system operations. A non-limiting example provides that input control devices may be assigned to workflow or image presentation functions, and may additionally be able to switch between these functions, such that each input option, whether by switch or menu selection or the like, may be mapped to a control input of a user workstation.

Input control devices configured according to embodiments presented herein may provide for positioning functions that are physically similar to functions that they represent, and are thus advantageous for certain operations. An illustrative and non-restrictive example provides that a trackball or mouse displacement motion and the stroke of a finger or stylus across a touch screen are apt for displacement and positioning inputs. Other non-limiting examples provide that rotation of a trackball bezel may resemble rotation of an item such as a slide and the rolling of a mouse roller in one direction or another may intuitively represent zoom-in and zoom-out. Such inputs may be configured to emulate operations that are familiar to users, such as pathologists experienced in operating optical microscopes, and are likely to be preferred over less intuitive arrangements that are also available, such as mapping an incremental change in position, rotation angle, or zoom to operation of a switch.

Input control devices may be used either by themselves (i.e., single device mode) or in combination with other devices (i.e., multiple device mode) in a digital image application configured according to embodiments. In a non-limiting example, a trackball input device may be used in combination with a digital pathology application in single device mode or in multiple device mode with a mouse input device. Continuing the example, in single device mode, the digital pathology application may automatically choose an appropriate mapping for an input device depending on, inter alia, default settings and user preferences. An illustrative and non-restrictive example provides for automatic mapping of a trackball device such that, in multiple device mode, the panning mode for a trackball component of a trackball input device is always on. As such, for example, when the mouse pointer is placed in an image viewing area, the trackball is in effect in continuous pan mode.

In general, FIGS. 8-15 demonstrate different modes in which workstations may be configured to operate with one or more input control devices and an associated set of mappings of switch and control inputs to functions configured according to embodiments. Input control device mappings depicted in FIGS. 8-15 may be configured as default mappings according to certain embodiments, which may be augmented by user defined mappings or preferences. In addition, FIGS. 8-11 generally provide examples of mappings arranged for a multiple device mode according to embodiments, including system operation using two distinct input devices associated with workflow and image presentation.

Figure 8:
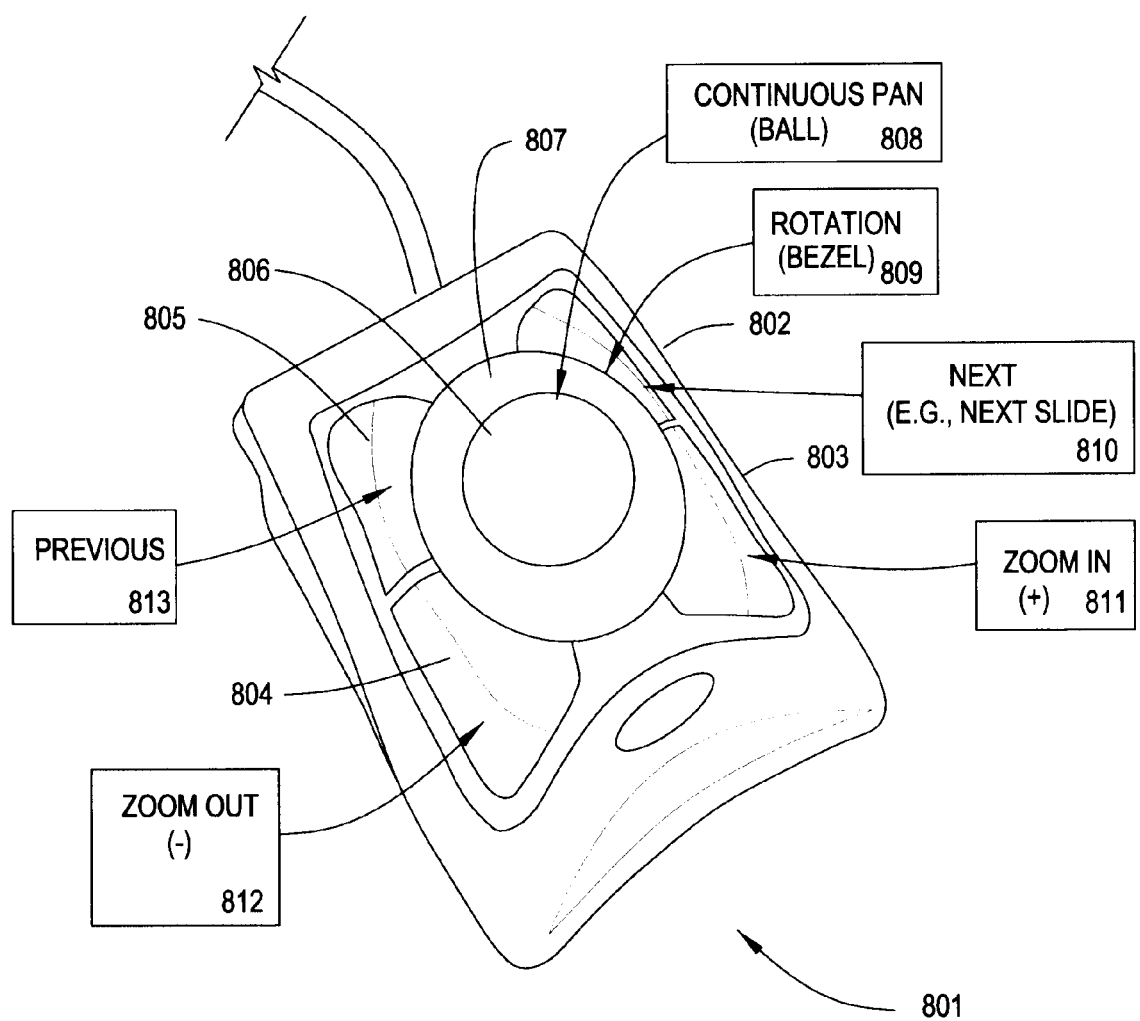
FIG. 8 provides an example manually operable input device configured for multiple device mode.

Referring to FIG. 8, therein is provided an example manually operable input device configured for multiple device mode according to an embodiment. The example manually operable input device 801 provided in FIG. 8 is a symmetrical trackball with surrounding intermittent push/release switch devices 802-805 associated with prospective mappings of switched inputs to functions. The input control device 801 may additionally be comprised of a trackball 806 surrounded by a bezel 807. The example illustrated in FIG. 8 provides the following device switch mappings: the upper right switch device 802 is mapped to a next image or slide 810 function, the lower right switch 803 is mapped to a zoom in 811 function, the lower left switch 804 is mapped to a zoom out 812 function, and the upper left switch 805 is mapped to a previous 813 function (e.g., access previous image). In addition, a continuous pan 808 function is mapped to the trackball 806, while a rotation 809 function is mapped to the bezel 807. This mapping configuration may be compared to FIG. 12, which provides an example mapping for a similar device operating in single input device mode arranged according to an embodiment.

Figure 9:
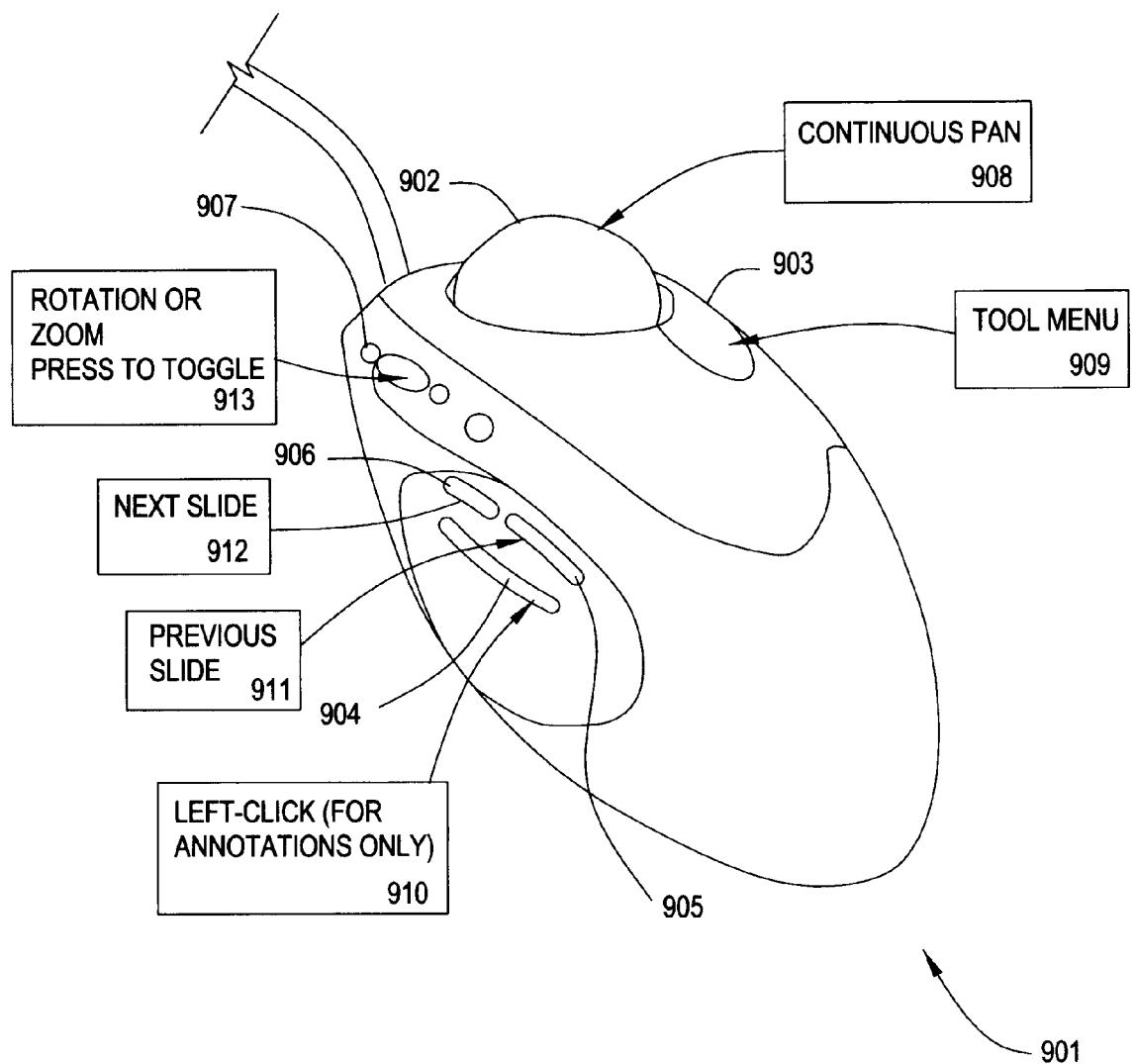
FIG. 9 provides another example manually operable input device mapped for multiple device mode.

FIG. 9 provides another example manually operable input device mapped for multiple device mode according to an embodiment. A right-handed mouse input device 901 is comprised of the following: a trackball 902 mapped to a continuous pan 908 function; a right selection switch 903 mapped to a tool menu 909 function; a bottom thumb-operated switch device 904 mapped to a left-click 910 function (for example, when performing image annotation); an upper right thumb-operated switch device 905 mapped to a previous slide 911 function; an upper left thumb-operated switch device 906 mapped to a next slide 912 function, and a finger-operated scroll wheel 907 mapped to multiple functions depending on the active operation, the functions including rotation, zoom, or press to toggle 913 functions.

According to embodiments, the functions mapped to the input device 901 elements may change depending on the operating environment or the active function. A non-limiting example provides that the trackball 902 may be used as a mouse-type pointer during certain functions, such as file navigation or during image annotation. An example of a similar device mapped for single device mode configured according to an embodiment is provided in FIG. 13.

Figure 10:
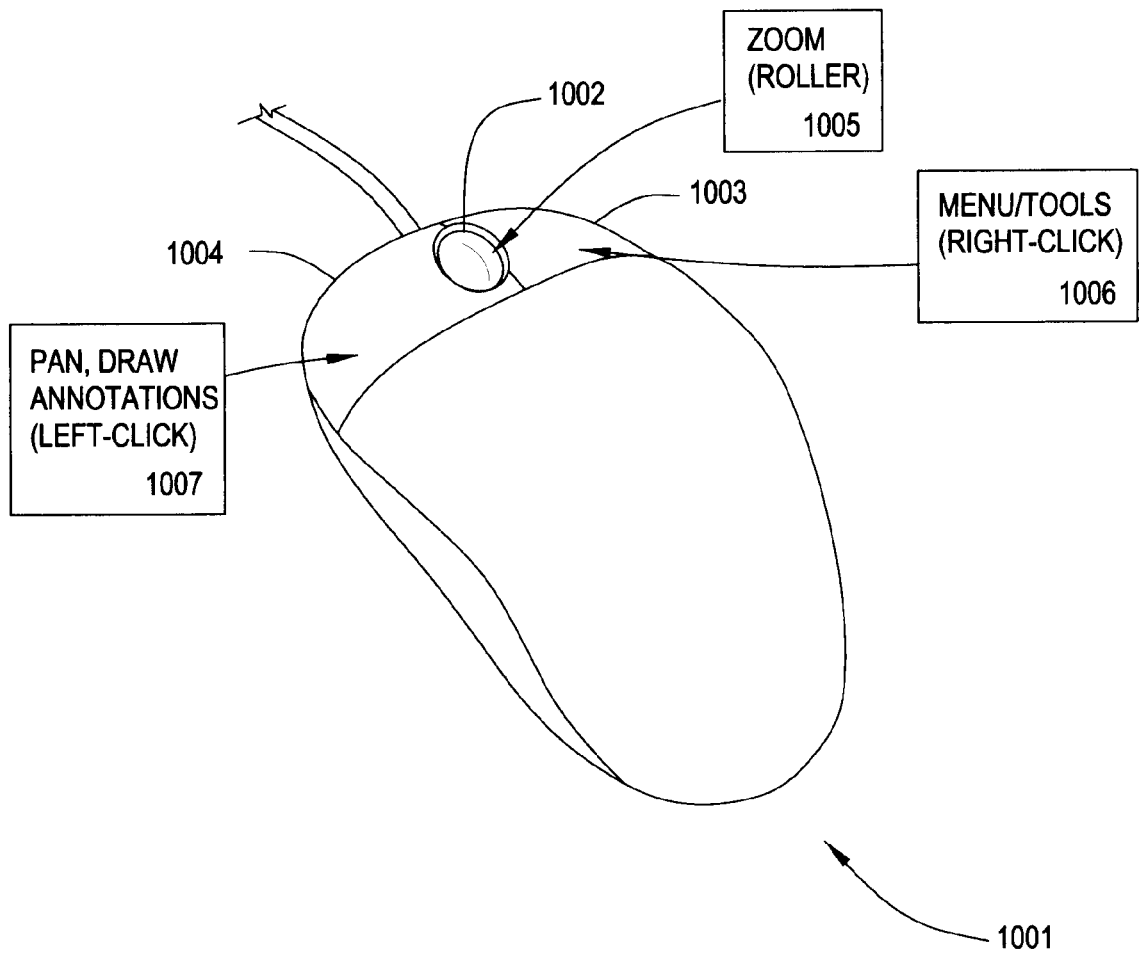
FIG. 10 provides an example of a simple mouse-type input device configured for multiple device mode.

An example of a simple mouse-type input device configured for multiple device mode according to an embodiment is provided in FIG. 10. The mouse-type input device 1001 provided in FIG. 10 is configured according to the following: a scroll wheel 1002 is mapped to a zoom (roller) 1005 function; a right-click button 1003 is mapped to a menu/tools 1006 function, and a left-click button 1004 is mapped to pan and draw annotations 1007 functions, depending on the active operation. Inasmuch as this device inherently has a limited number of switches, it may be advantageous for one of the switches to be mapped, especially when operating in a single input device configuration, to invoke a menu from which other functions may be selected, for example, as the right-click button 1003 is configured.

Figure 11A:
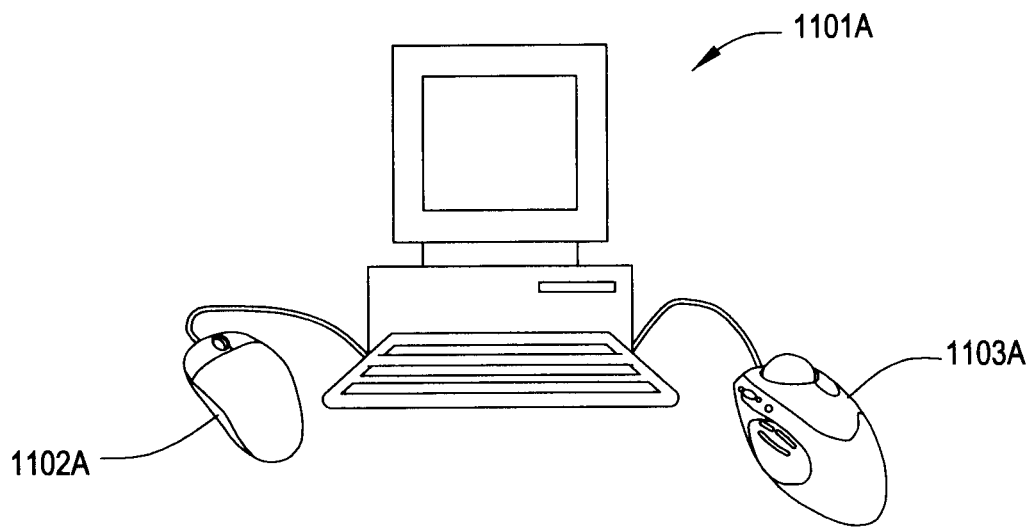
FIG. 11A provides an example workstation utilizing two input control devices.
Figure 11B:
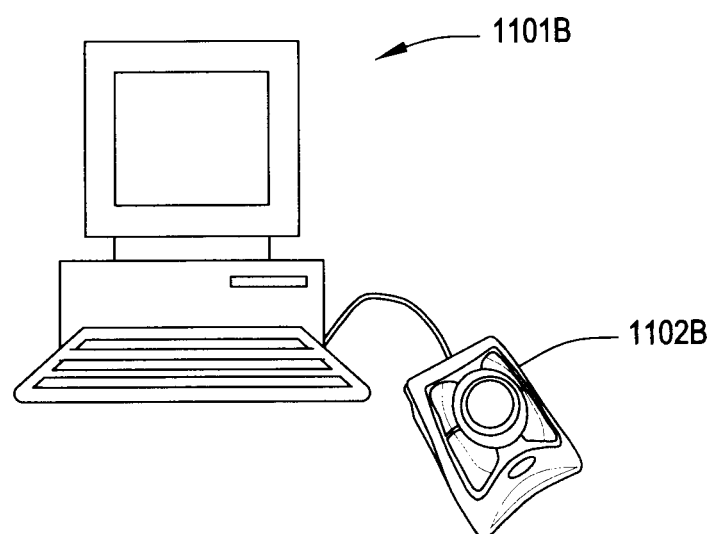
FIG. 11B provides an example workstation utilizing one input control device.

FIG. 11A illustrates an example workstation utilizing two input control devices according to an embodiment. Left and right input control devices 1102A, 1103A are connected to a workstation 1101A. The control input devices, illustrated as a typical mouse input device 1102A and an enhanced mouse input device 1103A with a trackball and multiple finger operated buttons, may be differentially mapped to certain functions as provided according to embodiments described herein. In this manner, the workstation may be configured to emulate certain functions, such as the operation of an optical microscope, and to provide differential control of functions, such as image manipulation using one device and information operations using the other device. FIG. 11B provides an example workstation configured to operate using a single input control device configured according to an embodiment. In the example provided in FIG. 11B, the input control device 1102B comprises a trackball input device operatively connected to the workstation 1101B.

Figure 12:
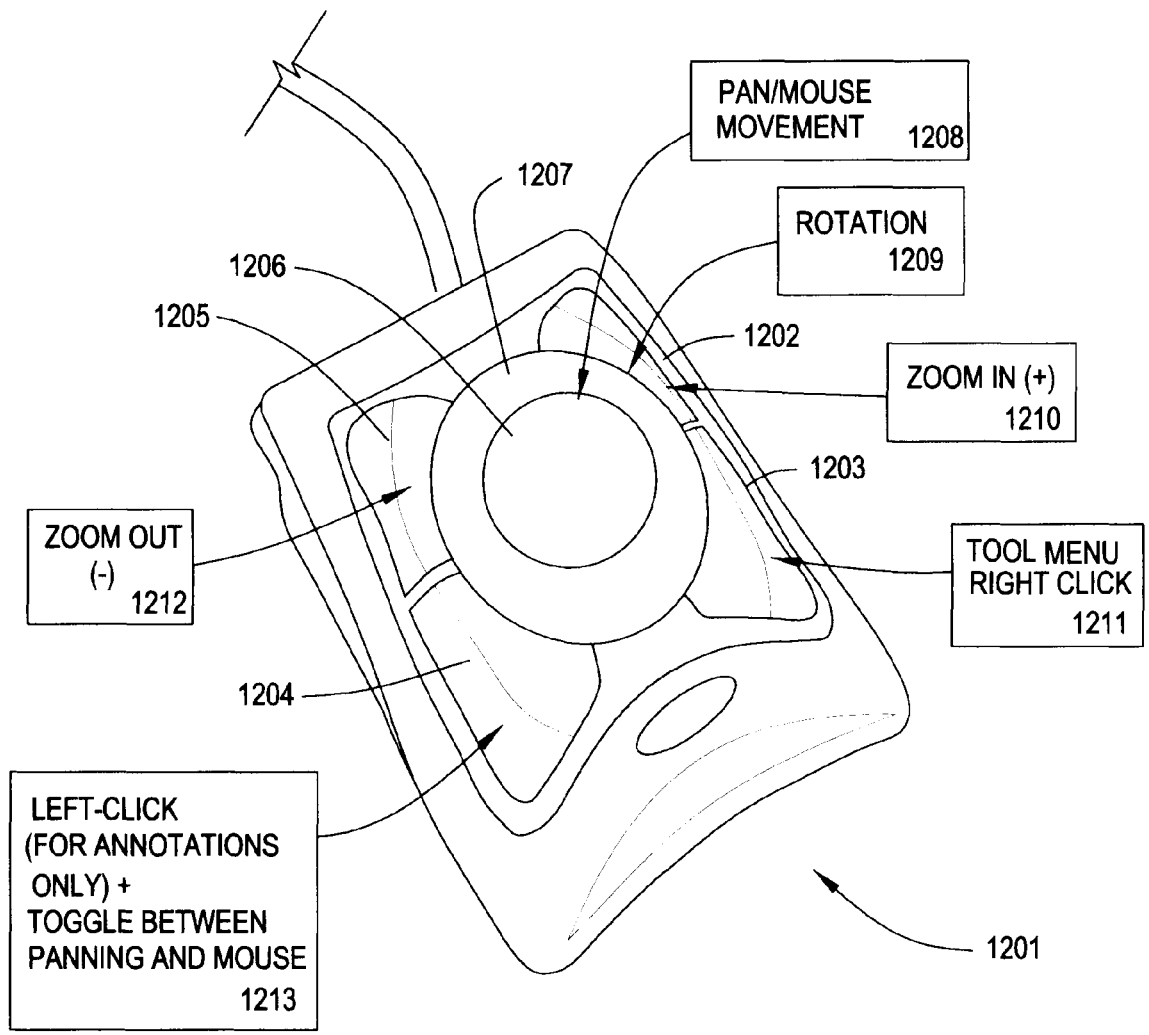
FIG. 12 provides an example manually operable input device configured for single input device mode according to an embodiment.

Referring to FIG. 12, therein is provided an example manually operable input device configured for single input device mode according to an embodiment. The example manually operable input device 1201 provided in FIG. 12 is a symmetrical trackball with surrounding intermittent push/release switch devices 1202-1205 associated with prospective mappings of switched inputs to functions. The input control device 1201 may additionally be comprised of a trackball 1206 surrounded by a bezel 1207. The example illustrated in FIG. 12 provides the following device mappings: the upper right switch device 1202 is mapped to a zoom in 1210 function, the lower right switch 1203 is mapped to tool menu and right-click 1211 functions, the lower left switch 1204 is mapped to left-click (e.g., for annotations), panning, and mouse 1213 functions, and the upper left switch 1205 is mapped to a zoom out 1212 function. Pan and movement 1208 functions may be mapped to the trackball 1206, while a rotation 1209 function may be mapped to the bezel 1207.

Figure 13:
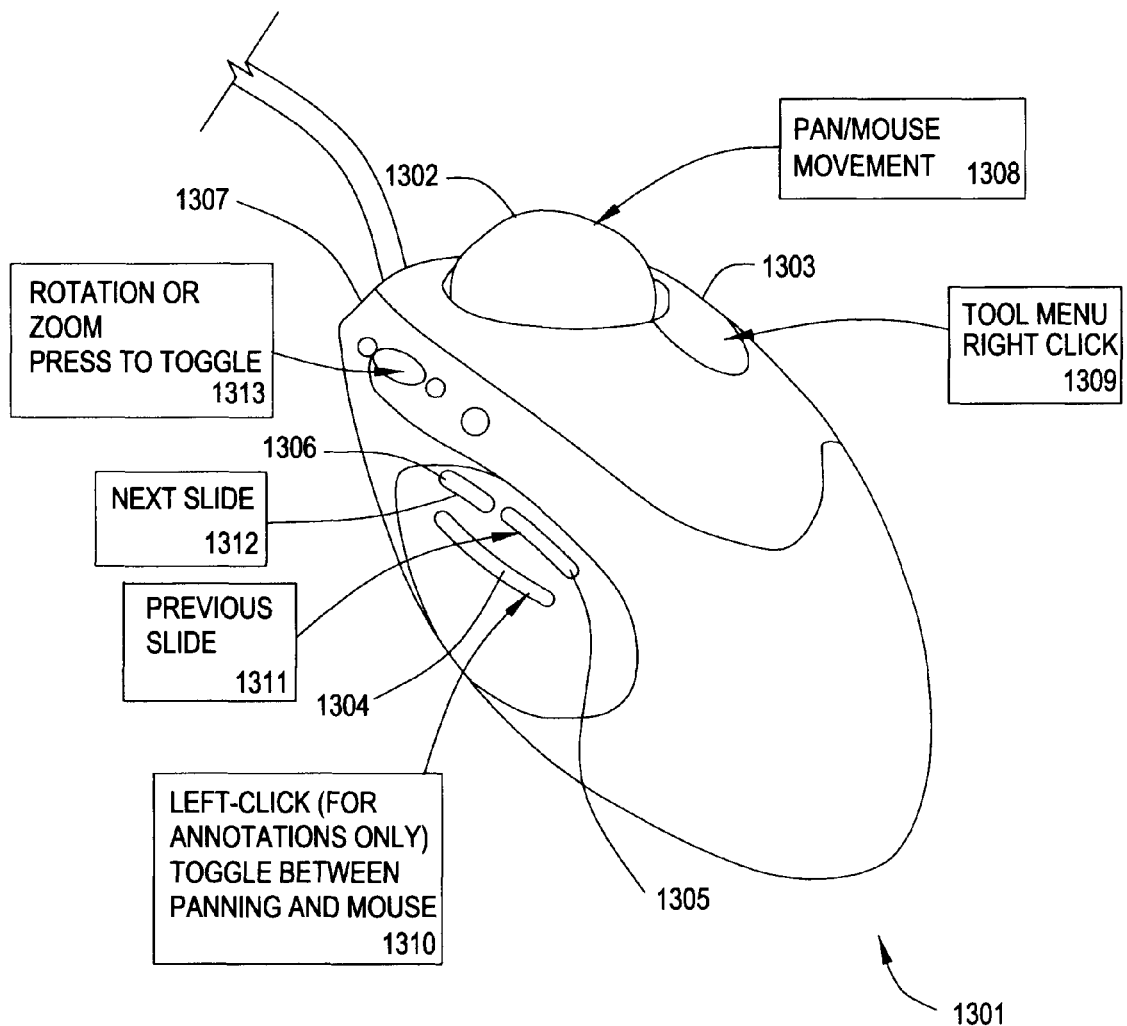
FIG. 13 provides another example manually operable input device configured for single device operational mode.

FIG. 13 provides an example manually operable input device configured for single device operational mode according to an embodiment. A right-handed mouse input device 1301 is comprised of the following: a trackball 1302 mapped to pan and mouse movement 1308 functions; a right selection switch 1303 mapped to tool menu and right-click 1309 functions; a bottom thumb-operated switch device 1304 mapped to left-click (e.g., for annotations), pan, and mouse 1310 functions; an upper right thumb-operated switch device 1305 mapped to a previous slide 1311 function; an upper left thumb-operated switch device 1306 mapped to a next slide 1312 function, and a finger-operated scroll wheel 1307 mapped to multiple functions depending on the active operation, the functions including rotation, zoom, or press to toggle 1313 functions. According to embodiments, the functions mapped to the input device 1301 elements may change depending on the operating environment or the active function.

Figure 14:
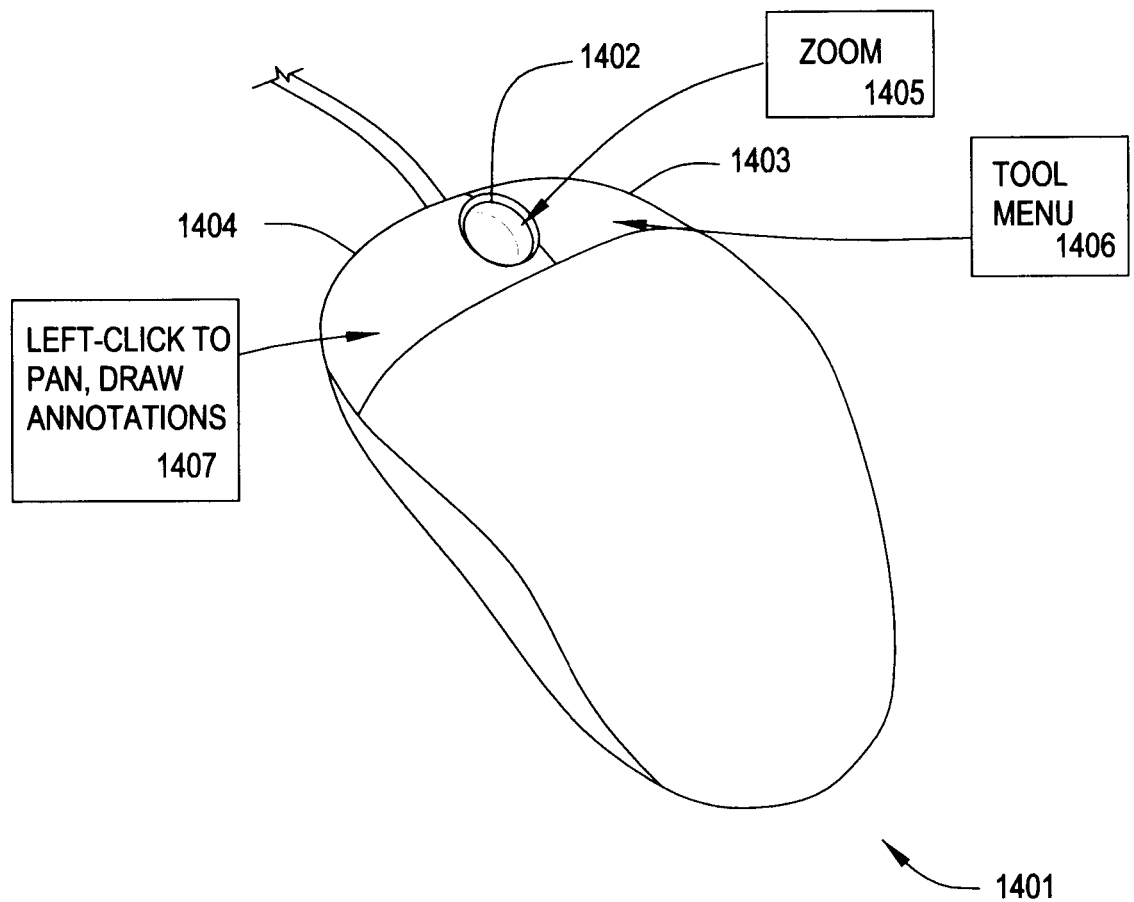
FIG. 14 provides an example simple mouse-type input device configured for single device mode.

Referring to FIG. 14, therein is provided an example simple mouse-type input device configured for single device mode according to an embodiment. The mouse-type input device 1401 is provided in FIG. 14 configured according to the following: a scroll wheel 1402 is mapped to a zoom 1405 function; a right-click button 1403 is mapped to a tool menu 1406 function, and a left-click button 1404 is mapped to pan and draw annotations 1407 functions, depending on the active operation.

Figure 15:
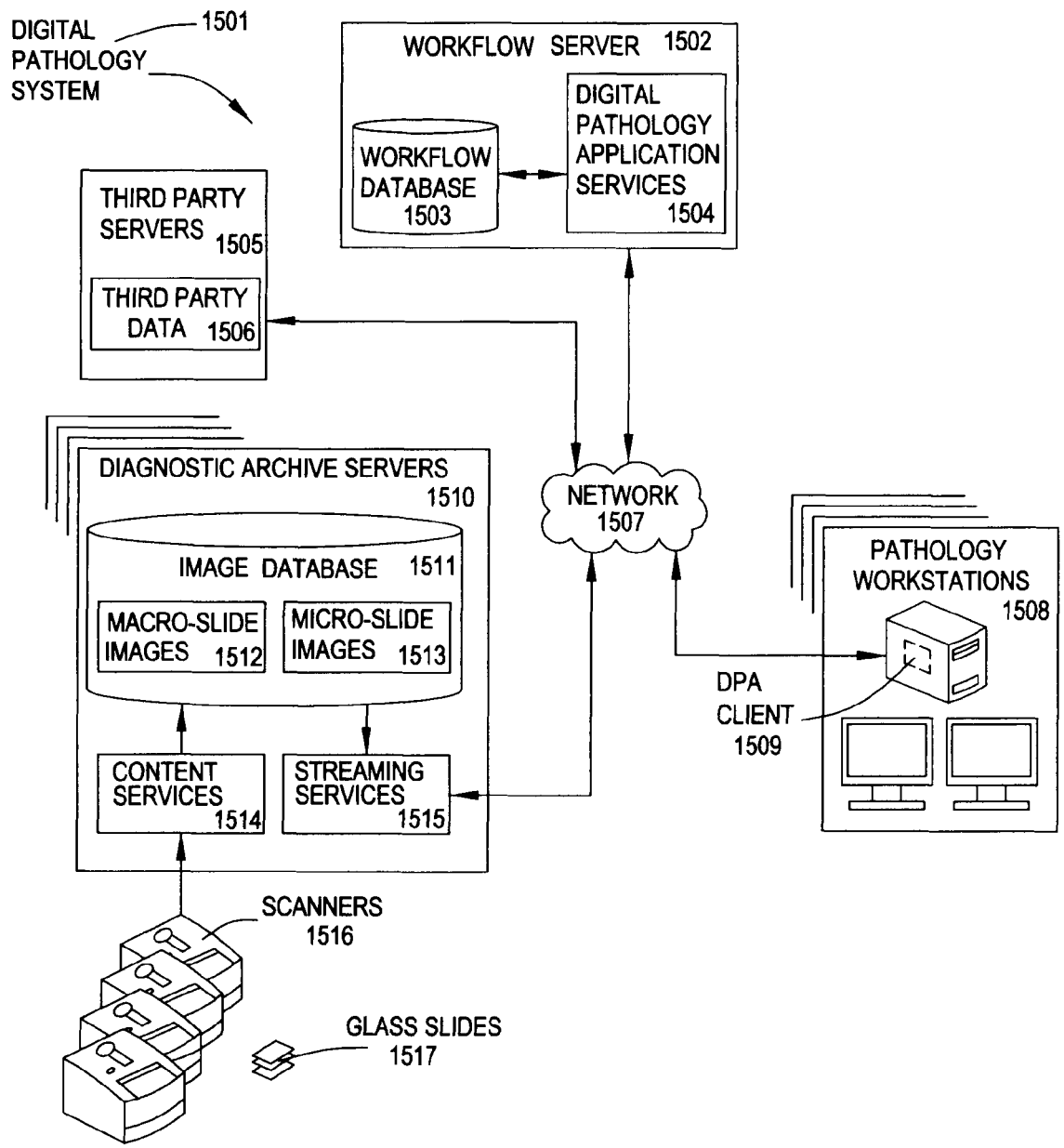
FIG. 15 provides an example digital pathology system.

FIG. 15 provides an example digital pathology system arranged according to an embodiment. A digital pathology system 1501 is provided that comprises a workflow server 1502, one or more third party servers 1505, a diagnostic archive server 1510, and pathology workstations 1508 arranged in a network 1507.

Digital specimen images may be generated by scanning prepared glass slides 1517 using scanners 1516 capable of transforming glass specimen slides into digital specimen images. As shown in FIG. 15, the digital specimen images may be stored on a diagnostic archive server 1510 in an image database 1511. A content services module 1514 may be utilized to manage the acquisition of digital specimen images, including macro-slide images 1512 and micro-slide images 1513. The outbound flow of digital specimen images to the network 1507 may be managed through one or more streaming services 1515. Digital specimen images may be accessed from an image database 1511 through digital pathology workstations 1508 running a digital pathology application (DPA) client 1509. The DPA client 1509 may provide navigation tools allowing a user, such as a pathologist, to view and manipulate digital slide images.

Third party data 1506, such as data available through a general Laboratory Information System (LIS) or a specialized Anatomic Pathology Laboratory Information System (APLIS), may be integrated with the digital specimen images. As illustrated in FIG. 15, the third party data 1506 may be supplied through third party servers 1505 operatively connected to the network 1507. A workflow server 1502 is provided that hosts application services 1504 for supporting one or more workstations 1508 operatively connected through a network 1507. The workflow server 1502 also includes a workflow database 1503 for storing data, including, but not limited to case data and information related to the digital pathology system, such as image catalog information for identifying the image server that is the source of the digital specimen images. One or more application services 1504 may be operational on the workflow server 1502. According to embodiments, application services 1504 may include functions directed toward assigning cases, managing case information and access thereto, managing images stored on the diagnostic archive servers 1510, providing reporting mechanisms, and facilitating data exchange between network 1507 components.

Figure 16:
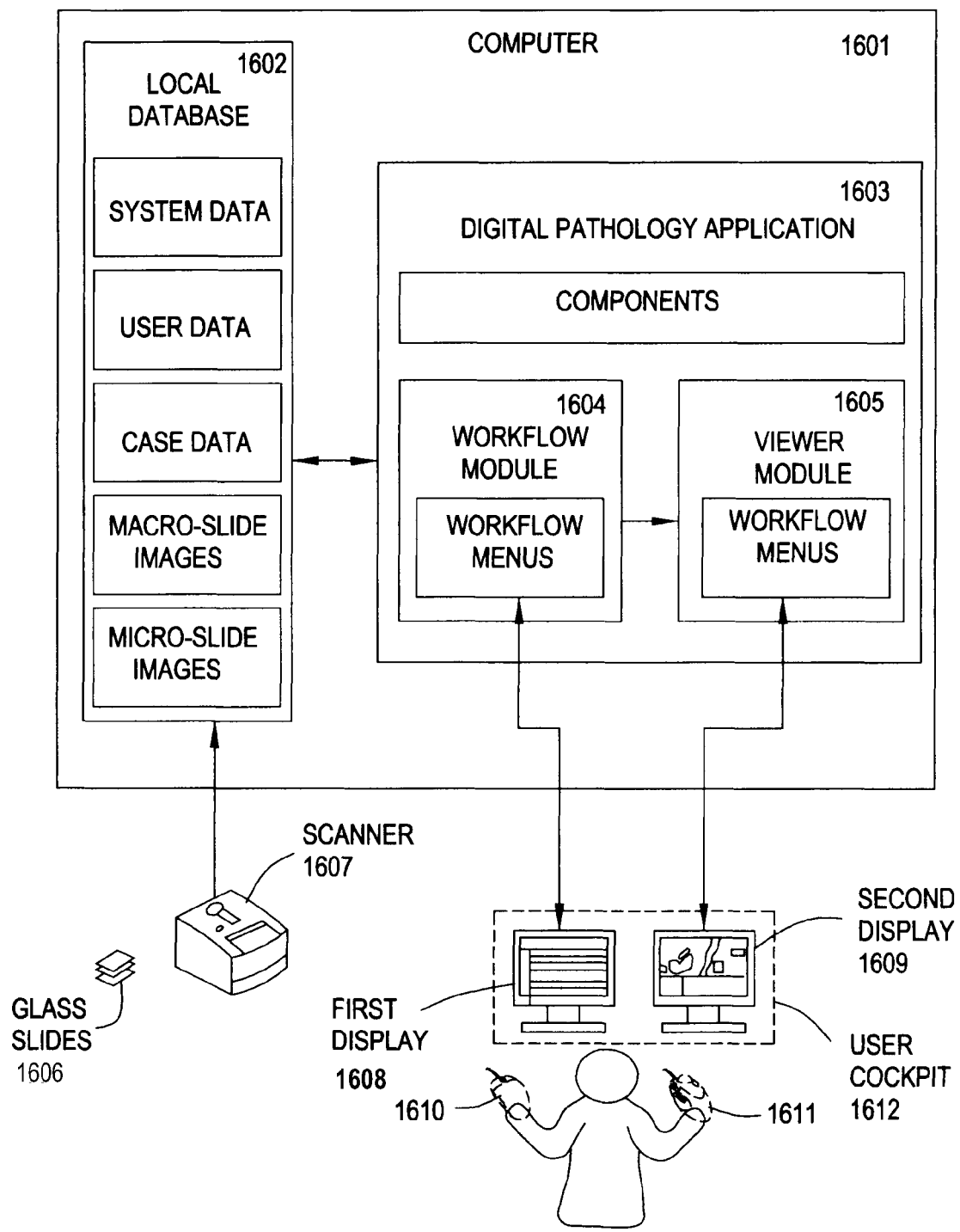
FIG. 16 provides an example digital image manipulation system.

FIG. 16 provides an example digital image manipulation system configured according to an embodiment. The system may be comprised of a computing device 1601, such as a desktop PC, server, or other information handling device, storing or accessing a data and image database 1602 and running a digital pathology application 1603. The digital pathology application 1603 may be further comprised of a workflow module 1604 and viewer module 1605, each providing a set of functions and menus. Digital images may be generated from glass slides 1606 using a digital scanner 1607 and transmitted to the database 1602.

A user may access the digital pathology application 1603 either by operating the computing 1601 operating the application or by running a client application at a remote computing device (not shown). In the example depicted in FIG. 16, multiple displays 1608, 1609 and multiple input control devices 1610, 1611 may be utilized to interact with the digital pathology application. The multiple displays 1608, 1609 may operate to create a "user cockpit" 1612 system for interacting with the digital pathology application 1603, wherein a first display 1608 and input device 1610 are dedicated to workflow module 1604 operations and a second display 1609 and input device 1611 are dedicated to viewer module 1605 (e.g., image manipulation) operations.

Figure 17:
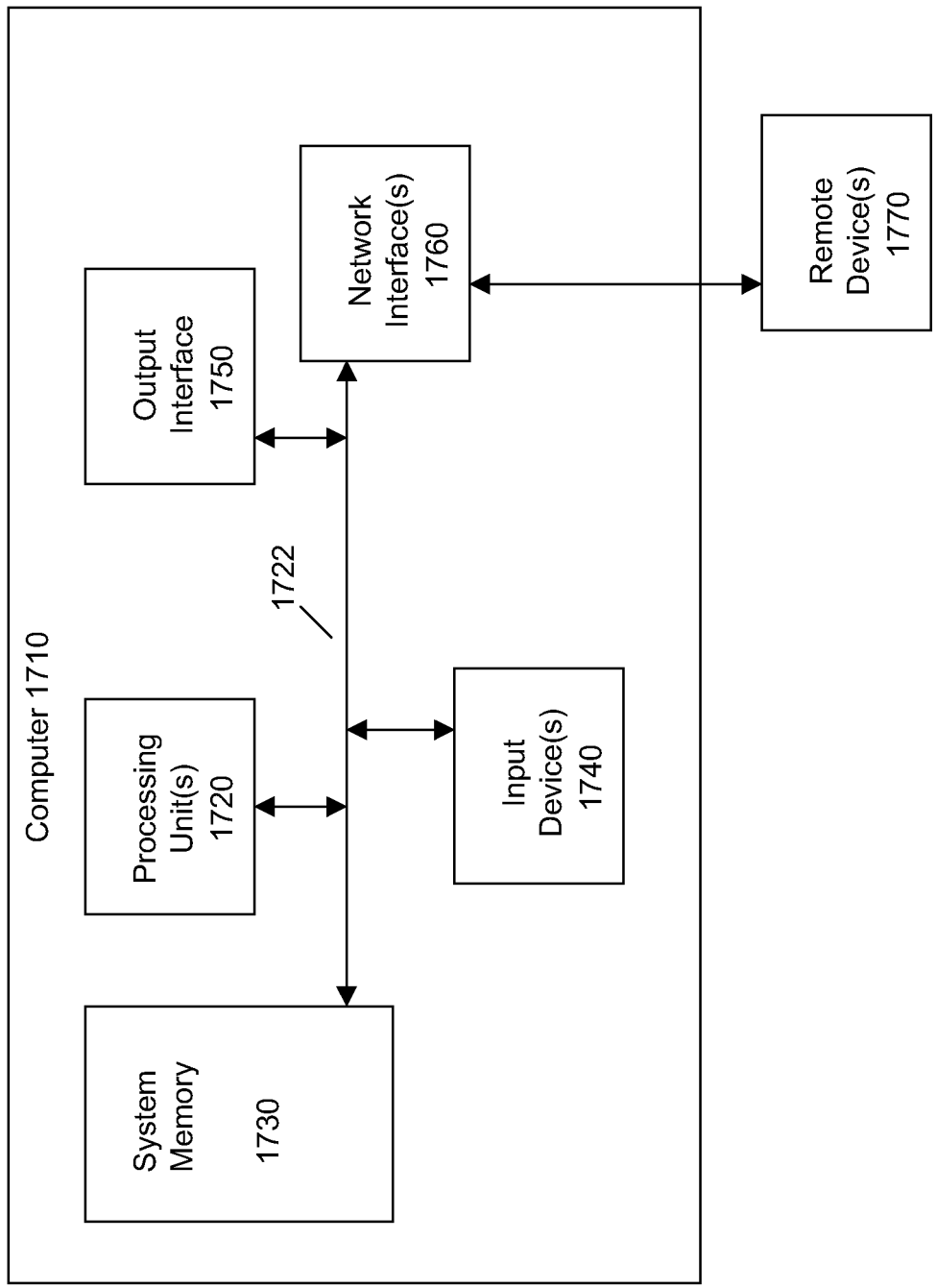
FIG. 17 illustrates an example circuitry of a computer system.

Referring to FIG. 17, it will be readily understood that certain embodiments can be implemented using any of a wide variety of devices or combinations of devices. An example device that may be used in implementing one or more embodiments includes a computing device in the form of a computer 1710.

Components of computer 1710 may include, but are not limited to, a processing unit 1720, a system memory 1730, and a system bus 1722 that couples various system components including the system memory 1730 to the processing unit 1720. The computer 1710 may include or have access to a variety of computer readable media. The system memory 1730 may include computer readable storage media in the form of volatile and/or nonvolatile memory such as read only memory (ROM) and/or random access memory (RAM). By way of example, and not limitation, system memory 1730 may also include an operating system, application programs, other program modules, and program data.

A user can interface with (for example, enter commands and information) the computer 1710 through input devices 1740. A monitor or other type of device can also be connected to the system bus 1722 via an interface, such as an output interface 1750. In addition to a monitor, computers may also include other peripheral output devices. The computer 1710 may operate in a networked or distributed environment using logical connections to one or more other remote computers or databases. The logical connections may include a network, such local area network (LAN) or a wide area network (WAN), but may also include other networks/buses.

It should be noted as well that certain embodiments may be implemented as a system, method or computer program product. Accordingly, aspects may take the form of an entirely hardware embodiment, an entirely software embodiment (including firmware, resident software, micro-code, et cetera) or an embodiment combining software and hardware aspects that may all generally be referred to herein as a "circuit," "module" or "system." Furthermore, aspects may take the form of a computer program product embodied in one or more computer readable medium(s) having computer readable program code embodied therewith.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, et cetera, or any suitable combination of the foregoing.

Computer program code for carrying out operations for various aspects may be written in any combination of one or more programming languages, including an object oriented programming language such as Java™, Smalltalk, C++ or the like and conventional procedural programming languages, such as the "C" programming language or similar programming languages. The program code may execute entirely on a single computer (device), partly on a single computer, as a stand-alone software package, partly on single computer and partly on a remote computer or entirely on a remote computer or server. In the latter scenario, the remote computer may be connected to another computer through any type of network, including a local area network (LAN) or a wide area network (WAN), or the connection may be made for example through the Internet using an Internet Service Provider.

Aspects are described herein with reference to flowchart illustrations and/or block diagrams of methods, apparatuses (systems) and computer program products according to example embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Although illustrated example embodiments have been described herein with reference to the accompanying drawings, it is to be understood that embodiments are not limited to those precise example embodiments, and that various other changes and modifications may be affected therein by one skilled in the art without departing from the scope or spirit of the disclosure.

What is claimed is:

1. A system comprising:
one or more processors;
a memory in operative connection with the one or more processors;
wherein, responsive to execution of program instructions accessible to the one or more processors, the one or more processors are configured to:
identify one or more input control devices in communication with a digital image application operating on said system, the one or more input devices comprising one or more control elements;
activate an input control device mode based on a number of identified input control devices; and
map the one or more control elements of each input control device to one or more digital image application functions based on a type of the input control device and the input control mode.

2. The system according to claim 1, wherein activation of the input control device mode comprises:
activating a single device mode responsive to identification of a single input control device operatively connected to said system; and
activating a multiple device mode responsive to identification of a plurality of input control devices operatively connected to said system.

3. The system according to claim 1, wherein the one or more processors are further configured to:
receive an input event initiated by an input control device at the digital image application; and
initiate an application function responsive to determining whether the input event targeted a mapped digital image application user interface element having a matching behavior.

4. The system according to claim 2, wherein a first input control device comprises a trackball input device.

5. The system according to claim 4, wherein a second input control device comprises a mouse input device.

6. The system according to claim 5, wherein the digital image application comprises a digital pathology application, the digital pathology application comprising a workflow module and a viewer module.

7. The system according to claim 6, wherein the trackball input device operates viewer module functions and the mouse input device operates workflow module functions of the digital pathology application.

8. The system according to claim 4, wherein the trackball input device comprises a trackball, bezel, and selector switch input control elements.

9. The system according to claim 8, wherein mapping comprises:
mapping the trackball control element to a continuous pan application function responsive to activation of the multiple device mode; and
mapping the trackball control element to a pan application function and a mouse movement function responsive to activation of the single device mode, the pan application function being active responsive to a cursor controlled by the trackball input device being over a digital image application user interface element.

10. The system according to claim 8, wherein the bezel control element is mapped to a rotation application function.

11. A method comprising:
identifying one or more input control devices in communication with a digital image application operating on a computing device comprising one or more processors operatively connected to a memory, the one or more input devices comprising one or more control elements;
activating an input control device mode based on a number of identified input control devices; and
mapping the one or more control elements of each input control device to one or more digital image application functions based on a type of the input control device and the input control mode.

12. The method according to claim 11, wherein activation of the input control device mode comprises:
activating a single device mode responsive to identification of a single input control device operatively connected to said computing device; and
activating a multiple device mode responsive to identification of a plurality of input control devices operatively connected to said computing device.

13. The method according to claim 11, further comprising:
receiving an input event initiated by an input control device at the digital image application; and
initiating an application function responsive to determining whether the input event targeted a mapped digital image application user interface element having a matching behavior.

14. The method according to claim 12, wherein a first input control device comprises a trackball input device.

15. The method according to claim 14, wherein a second input control device comprises a mouse input device.

16. The method according to claim 15, wherein the digital image application comprises a digital pathology application, the digital pathology application comprising a workflow module and a viewer module.

17. The method according to claim 16, wherein the trackball input device operates viewer module functions and the mouse input device operates workflow module functions of the digital pathology application.

18. The method according to claim 14, wherein the trackball input device comprises a trackball, bezel, and selector switch input control elements.

19. The method according to claim 18, wherein mapping comprises:
mapping the trackball control element to a continuous pan application function responsive to activation of the multiple device mode; and
mapping the trackball control element to a pan application function and a mouse movement function responsive to activation of the single device mode, the pan application function being active responsive to a cursor controlled by the trackball input device being over a digital image application user interface element.

20. A computer program product comprising:
a non-transitory computer readable storage medium having computer readable program code embodied therewith, the computer readable program code comprising:
computer readable program code configured to identifying one or more input control devices in communication with a digital image application, the one or more input devices comprising one or more control elements;
computer readable program code configured to activate an input control device mode based on a number identified input control devices; and
computer readable program code configured to map the one or more control elements of each input control device to one or more digital image application functions based on a type of the input control device and the input control mode.

* * * * *